United States Patent
Huber et al.

(10) Patent No.: US 10,959,605 B2
(45) Date of Patent: Mar. 30, 2021

(54) DEVICE FOR SIMULTANEOUS FIXATION OF MEDICAL INSTRUMENTS AND CORRESPONDING SYSTEM

(71) Applicant: KARL STORZ SE & Co. KG, Tuttlingen (DE)

(72) Inventors: Florian Huber, Tuttlingen (DE); Werner Goebel, Tuttlingen (DE); Bernhard Gloeggler, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 0 days.

(21) Appl. No.: 16/938,949

(22) Filed: Jul. 25, 2020

(65) Prior Publication Data
US 2021/0038057 A1 Feb. 11, 2021

(30) Foreign Application Priority Data
Aug. 7, 2019 (DE) .................. 10 2019 121 360

(51) Int. Cl.
*A61B 1/00* (2006.01)
*A61B 17/34* (2006.01)
(Continued)

(52) U.S. Cl.
CPC ...... *A61B 1/00149* (2013.01); *A61B 1/00154* (2013.01); *A61B 17/00234* (2013.01);
(Continued)

(58) Field of Classification Search
CPC . A61B 1/00149; A61B 1/00154; A61B 90/50; A61B 90/57; A61B 2017/0047;
(Continued)

(56) References Cited

U.S. PATENT DOCUMENTS

2012/0296281 A1   11/2012  Jaspers et al.
2014/0005484 A1*  1/2014   Charles .............. A61B 1/00009
                                                         600/201
(Continued)

FOREIGN PATENT DOCUMENTS

DE    102018103968 A1    8/2019
NL    9402207 A          8/1996
(Continued)

OTHER PUBLICATIONS

German Search Report (Including Translation) for German Patent Application No. 10 2019 121 360.6, dated Apr. 14, 2020.
(Continued)

*Primary Examiner* — Ashley L Fishback
(74) *Attorney, Agent, or Firm* — Jason H. Vick; Sheridan Ross, PC

(57) ABSTRACT

A device for simultaneous fixation of medical instruments is disclosed, the device comprising a holding portion, a coupling element and a pushing element, wherein the coupling element is configured for the holding portion to be pivoted about a pivot axis, and the pushing element is configured, in a first position, not to exert a force or a first force on the holding portion so that the holding portion can be pivoted, and, in a second position, to exert a second force, which is greater than the first force, on the holding portion so that the holding portion can be pivoted with respect to the first force. is fixed with respect to rotation about the pivot axis. A system with such a device is also disclosed.

17 Claims, 3 Drawing Sheets

Figure 1:
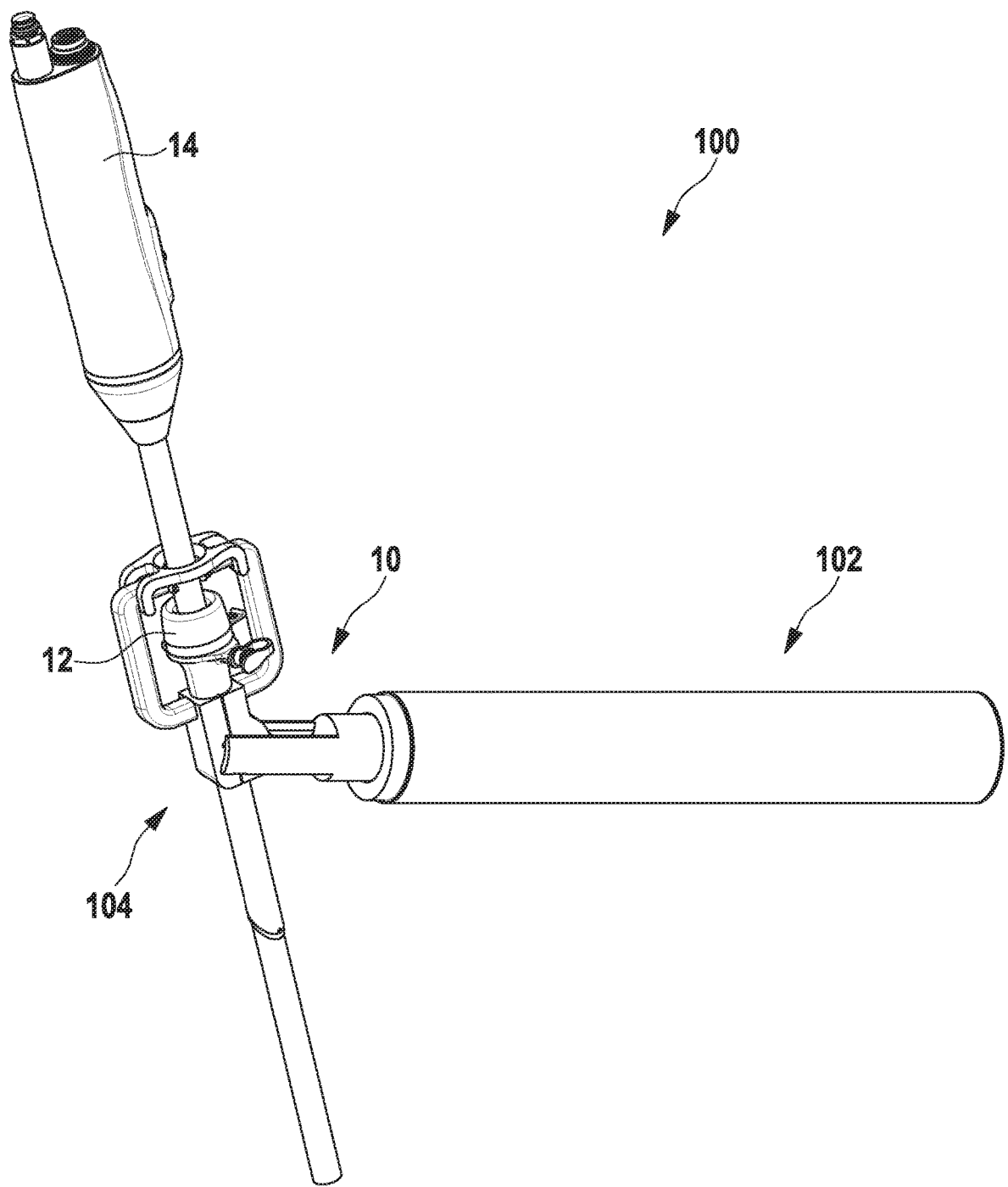

(51) Int. Cl.
*A61B 90/57* (2016.01)
*A61B 17/00* (2006.01)

(52) U.S. Cl.
CPC ...... *A61B 17/3403* (2013.01); *A61B 17/3478* (2013.01); *A61B 90/57* (2016.02); *A61B 2017/00477* (2013.01); *A61B 2017/3405* (2013.01); *A61B 2017/347* (2013.01); *A61B 2017/3445* (2013.01)

(58) Field of Classification Search
CPC ...... A61B 2017/347; A61B 2017/3445; A61B 2017/00234
See application file for complete search history.

(56) References Cited

U.S. PATENT DOCUMENTS

2015/0366627 A1* 12/2015 Oginski ................. A61B 90/50
248/288.11
2019/0254773 A1 8/2019 Goebel et al.

FOREIGN PATENT DOCUMENTS

WO     WO 01/54560     8/2001
WO     WO 2016/144180     9/2016

OTHER PUBLICATIONS

European Search Report for European Application No. 20176747.2, dated Nov. 5, 2020.

* cited by examiner

DEVICE FOR SIMULTANEOUS FIXATION OF MEDICAL INSTRUMENTS AND CORRESPONDING SYSTEM

CROSS REFERENCE TO RELATED APPLICATIONS

This application claims priority to German Patent Application 10 2019 121 360.6, filed Aug. 7, 2019, the entire contents of this priority application are incorporated herein by reference.

The present disclosure concerns a device for the simultaneous fixation of medical instruments and a system comprising such a device.

The positioning of medical instruments in clinical routine is still done manually or with special holding arm systems. The positioning of an instrument introduced into a trocar is of particular interest. Reference is made to the publication US 2012/0296281 A1 as an example.

One of the requirements for positioning can be a possibility of quickly positioning in an axial direction, i.e. along a longitudinal axis of coupling, especially the endoscope axis. Furthermore, a rotation possibility around a puncture site, especially a trocar puncture, is often desired. The pivot or pivot point is preferably chosen in the immediate vicinity of the puncture site in order to avoid mechanical stress, in particular strain, at the puncture site in the event of displacement.

WO 2016/144180 A1 shows a customized trocar with a compressible ball joint. The ball joint is equipped with a compression strap which compresses a ball of the ball joint when the strap is contracted, thus achieving fixation of an instrument inserted into the trocar. However, one of the desired features that remains is that the device used for holding should be more flexible with regard to different instruments, especially with regard to instrument diameter.

For solutions that do not require a holding arm system, manual positioning of the endoscope or instrument can be done quickly and according to the situation, but requires an additional person in the sterile area in an operating room to hold the endoscope or instrument. Usually the endoscope is held and guided accordingly while the surgeon performs his interventions with further instruments (introduced by further trocars) under the field of view of the endoscope.

Holding arm systems, on the other hand, allow the endoscope or instrument to be fixed in place, whereby the holding arm can also be released by the surgeon himself if necessary. However, this usually requires an intervention in the surgeon's workflow. In addition, the holding arm mechanism usually has to be completely released, so that repositioning usually equals a relatively time-consuming, complete repositioning of the holding arm. This repositioning usually requires both hands of the surgeon or assistant, so that they have to interrupt their current activities.

The inventors have therefore recognized the need for an easy-to-release holding system for endoscopes or instruments inserted into the trocar, which allows the endoscope or instrument to be moved along a longitudinal center axis, the z-axis, and to be shifted or rotated about a pivot point near the trocar puncture.

In principle, the holding system should be independent of the trocar and endoscope or instrument used, e.g. with regard to different diameters or lengths, so that it can be used for a variety of possible combinations, especially of trocar and endoscope.

It is an object to provide a device for the simultaneous fixation of medical instruments, which allows the holding of instruments with different diameters and can be operated with one hand. Furthermore, a corresponding system with two medical instruments shall be shown.

According to a first aspect there is provided a device for the simultaneous fixation of medical instruments, the device having a holding portion comprising two holding elements, a coupling element, and a pushing element, the coupling element being configured for the holding portion to be moved about a pivot axis, in particular in a pivot plane, and the pushing element is configured to exert no force or a first force on the holding portion in a first position so that the holding portion can be pivoted and to exert a second force greater than the first force on the holding portion in a second position so that the holding portion is fixed regarding a rotation around the pivot axis, said holding portion comprising a continuous cavity having a longitudinal center axis and being configured to receive a first medical instrument along said longitudinal center axis, each of said holding members comprising a base member and an arm member, wherein each arm member in a first arm section starting from the base member extends away from the longitudinal center axis, in a second arm section approaches the longitudinal center axis and ends with a support surface, thereby forming a free space between the arm members which is configured to receive a second medical instrument along the longitudinal center axis.

Such a device may enable the surgeon to easily reposition the holding portion and thus change the position of the medical instruments. For this purpose, the pushing element may be moved and/or rotated between at least the two positions mentioned. In the first position the pushing element exerts no or only a small force on the holding portion. As a result, the holding portion may be moved freely relative to the coupling element or moved with little resistance. This first position may therefore be used to position or reposition the holding portion for the first time. The pivot axis is established, in some exemplary embodiments, by having the holding portion being pivotably mounted at two or more than two points.

In the second position, the pushing element exerts a greater second force on the holding portion. On the one hand, this results in greater friction, especially static friction, between the pushing element and the holding portion. On the other hand, the holding portion is also pressed against its bearing, which also increases the friction at this location. This increase in friction means that the holding portion is fixed at least in the degree of freedom around the pivot axis, here called rotation. The second position is therefore used if the holding portion is positioned as desired and its position is not to be changed any more with respect to the degree of freedom around the pivot axis, i.e. especially in the pivot plane.

It should also be noted that when using a holding arm, the support section may also rotate around a longitudinal axis of the holding arm when the pushing element is in the first position. It is also possible to hold other second medical instruments instead of an endoscope, such as forceps or scissors.

In an exemplary embodiment, it is also possible to effect whether one, two or more of the medical instruments may be moved along the longitudinal center axis by varying the position of the pushing element.

On the one hand, the holding elements may be configured in such a way that in the first position they allow a displacement of the first medical instrument guided therein, but not in the second or another third position. This follows from the fact that the two holding elements exert less force on the first medical instrument in the cavity than in the second or third position. In an exemplary embodiment, friction, in particular static friction, may again cause the first medical instrument to be fixed when a greater force is applied. In particular, the holding portion is pivoted in a pivot plane that is perpendicular to the pivot axis. The holding portion is then also fixed in the pivot plane with respect to rotation about the pivot axis. In an exemplary embodiment, the first instrument is alternatively or additionally held positively.

In another exemplary embodiment, the arm elements with their contact surfaces in the second or third position exert a force on the second medical instrument, either directly through a physical contact or indirectly via an intermediate element.

While in the first position the force exerted by the arm elements is still small and allows the second medical instrument to be displaced along the longitudinal center axis, in the second or third position the arm elements are pressed against the second medical instrument in the direction of the longitudinal center axis in such a way that the now increased friction, in particular static friction, prevents the second medical instrument from being displaced along the longitudinal center axis.

In another exemplary embodiment, a third force in the third position is greater than the second force.

In this way it may be possible that in the first position of the pushing element both the medical instruments along the longitudinal center axis may be displaced and the holding portion may be displaced around the pivot axis. In the second position, the pushing element presses against the holding portion and fixes it with respect to a rotation around the pivot axis, but a displacement of the medical instruments along the longitudinal center axis is still possible. At the greatest third force, the two holding elements are pressed together and thus pressed against the medical instruments in such a way that both the medical instruments are now fixed along the longitudinal center axis and the holding portion is fixed with respect to rotation about the pivot axis.

In another exemplary embodiment, the third force in the third position is greater than the first force but less than the second force.

This embodiment may enable the medical instruments to be moved along the longitudinal center axis in the first position and the holding portion to be pivoted about the pivot axis. In the third position with the third force, the pushing element presses the two holding elements together and thus presses them against the medical instruments in such a way that they are fixed along the longitudinal center axis. Finally, in the second position, the holding portion is also fixed with respect to rotation about the pivot axis.

In another exemplary embodiment, a fourth force may also be applied in a fourth position, whereby in the first position with the first force all elements, i.e. the holding portion, the first medical instrument and the second medical instrument, may be displaced or pivoted, in a third position all elements may be displaced or pivoted except for one, in the fourth position all elements except for one are fixed, and finally in the second position all elements are fixed.

This possibility of step-by-step fixing may be achieved by influencing the corresponding frictional forces by appropriate embodiment of the elements, including the choice of materials and surfaces. For this purpose, on the one hand, the friction between the holding portion and the combination of coupling element and pushing element, the friction between the holding portion and the first medical instrument, and the friction between the bearing surfaces or an intermediate piece arranged on the bearing surfaces and the second medical instrument are adjusted by embodiment.

In another exemplary embodiment, the coupling element has a degree of freedom so that the coupling element may be rotated about its longitudinal axis, hereinafter referred to as the longitudinal axis of coupling, or about an axis perpendicular to the pivot axis.

This rotation may usually take place in relation to a holding arm. Since the holding portion is held by the coupling element, the holding portion may be moved even more flexibly, namely on the one hand around the pivot axis and on the other hand in a plane of rotation which is created during a rotation around the longitudinal axis of coupling element.

In another exemplary embodiment, the displacement of the pushing element, either to one of the above-mentioned positions or to a fifth position, may cause the coupling element to be fixed with respect to its rotation about its longitudinal axis.

This is because if the pushing element presses against the holding portion, the holding portion may also press against the coupling element due to its bearing on the coupling element. If, for example, the coupling element is pressed against a surface due to this force, in some exemplary embodiments against a conical surface, the friction between the coupling element and this surface may cause the coupling element to be fixed relative to this surface and to no longer be able to rotate about its longitudinal axis of coupling. In this way, a very high degree of flexibility may be achieved in the positioning of medical instruments.

In another exemplary embodiment, it is possible in the first position to move or rotate the holding portion around the pivot axis, to move the medical instruments along the longitudinal center axis and to rotate the coupling element around its longitudinal axis of coupling.

In the second position, the holding portion is fixed with respect to rotation about the pivot axis, the medical instruments are fixed along the longitudinal center axis and the coupling element is fixed with respect to its longitudinal axis of coupling.

In another exemplary embodiment, the pushing element is configured to press a first holding element of the holding elements against a second holding element of the holding elements, whereby the bearing surface of the first holding element and the bearing surface of the second holding element also move towards each other.

This embodiment allows the medical instruments to be fixed relative to the holding portion. Depending on the embodiment of the holding portions and the contact surfaces, it is also possible to set whether only the first medical instrument or only the second medical instrument is fixed at a certain predetermined force or whether both medical instruments are fixed essentially simultaneously.

In another exemplary embodiment, the device further comprises a guide element having an opening which is perpendicular to the longitudinal center axis and the guide element is in contact with the bearing surfaces when the second force is applied to the holding portion.

This embodiment may make it particularly easy to adjust the device to second medical instruments with different diameters. For some exemplary embodiments, the contact surfaces lie directly against the second medical instrument and hold and/or fix it. If the arm sections have a certain flexibility, it is even possible to use second medical instruments with different diameters. In this case, the guide element offers further possibilities for adaptation to a wide range of different diameters of the second medical instrument. The embodiment of the guide element is chosen in such a way that the guide element on the one hand rests on the bearing surfaces and on the other hand, at least when the pushing element is in the second position, also rests on the second medical instrument. A force exerted by the contact surfaces is then transferred to the second medical instrument via the guide element. The guide element may be used, in some exemplary embodiments, if direct contact between the bearing surfaces and the second medical instrument is not desired. In some exemplary embodiments, the guide element may be clipped to the contact surfaces and/or to the second arm sections. In this way, the guide element may be replaced very easily.

In another exemplary embodiment, the coupling element has two projections which are parallel to each other and between which the pushing element is guided.

This embodiment may allow for a good support of the holding portion. In particular, good guidance of the holding portion around the pivot axis may be ensured.

In another exemplary embodiment, the coupling element has two recesses which face each other, and wherein the holding portion has a projection on each of two opposite sides which engages in one of the recesses.

This embodiment may make it easy to implement the bearing of the holding portion on the coupling element.

In another exemplary embodiment, the coupling element has two projections facing each other, and wherein the holding portion has a recess on each of two opposite sides, in which one of the projections engages.

This embodiment may make it easy to implement the bearing of the holding portion on the coupling element.

In another exemplary embodiment, the recesses have a slot which is configured in such a way that the holding portion may be pushed out of the recesses perpendicular to the pivot axis.

This embodiment may allow to easily relocate the device, especially for feeding it to a disinfection process and/or an autoclaving process. The recess and slot are arranged, in some exemplary embodiments, in such a way that the holding portion is held during operation in an area of the coupling element where the recesses cannot enter the slot and therefore cannot be pushed out of the slot.

In another exemplary embodiment, the longitudinal center axis intersects the pivot axis.

This embodiment may create a point, namely the intersection of the longitudinal center axis and the pivot axis, in particular a pivot point, which remains unchanged both when the holding portion is moved around the pivot axis and when the coupling element is rotated around its longitudinal axis. Then, among other things, if this intersection point lies close to the location of the trocar puncture during an operation, a displacement of the holding portion about the pivot axis and/or a rotation of the coupling element have only a small effect with respect to a displacement of the location of the trocar puncture.

In another exemplary embodiment, the device also has a holding arm by which the pushing element is held when the second force is applied, the coupling element having a flange which is attached to the holding arm by a union element.

This embodiment may make it possible to arrange the coupling element so that it may rotate in relation to the holding arm and at the same time fix the pushing element to fix the coupling element with regard to its rotational movement. The union element is attached to the holding portion and the flange of the coupling element is located below the union element. If the pushing element now presses against the holding portion, the holding portion also presses against the coupling element. This causes the flange of the coupling element to be pressed against the union element. The resulting friction, especially static friction, between the flange and the union element blocks rotation of the coupling element about its longitudinal axis. In some exemplary embodiments the union element is attached to the holding arm by means of a thread or a bayonet lock. This may make it possible to easily separate the coupling element from the holding arm and then to feed both the union element and the coupling element to a disinfection process and/or an autoclaving process. In particular, the union element may be configured as a union nut.

In another exemplary embodiment, the pushing element is coupled to the holding arm via a ball joint.

This embodiment may allow the pushing element to be rotated together with the coupling element around the longitudinal axis of the coupling.

In another exemplary embodiment, a first one of the holding elements has a recess and a second one of the holding elements has a projection, the projection engaging in the recess when the second force is applied to the holding portion.

This embodiment may allow to mount only one of the holding elements on the coupling element, whereas the other holding element is held in place by the interaction of projection and recess. Since the pushing element rests against the other holding element during operation, the holding elements do not come loose from each other.

In another exemplary embodiment, each arm element has a third arm section which is located between the first arm section and the second arm section and extends at least substantially parallel to the longitudinal center axis.

This embodiment may allow for a compact construction, but still provides good access to the medical instruments, especially the first medical instrument.

In another exemplary embodiment, the first arm section and the second arm section are each at least substantially perpendicular to the third arm section.

This embodiment may allow for a compact construction, but still provides good access to the medical instruments, especially the first medical instrument.

In another exemplary embodiment, an elastic holding element is inserted into the holding portion, which is configured to accommodate a first instrument of the medical instruments along the longitudinal axis of the coupling.

This embodiment may enable the first instruments with different diameters to be used in a simple way. If such an elastic holding element is used, the holding portions press against the first medical instrument via the elastic holding element and thus fix it along the longitudinal center axis. Such an elastic holding element, in some exemplary embodiments, may have the shape of a cylinder jacket, especially with a flange to prevent slipping.

In another exemplary embodiment, the holding portion is configured to guide a trocar and the contact surfaces are configured to hold an endoscope inserted into the trocar.

Since the instruments are held in different places, a particularly good individual positioning and fixation may be possible. This embodiment may be especially configured to a typical application. For this purpose, the inner diameter of the cavity is, in some exemplary embodiments, between 5 and 15 millimeters, in other exemplary embodiments, between 7 and 13 millimeters and, in some further exemplary embodiments, between 8 and 12 millimeters. The outer diameter of the endoscope may at least be slightly smaller than the inner diameter of the trocar and is, in some exemplary embodiments, smaller than 10 millimeters, in other exemplary embodiments, smaller than 7 millimeters and, in some further exemplary embodiments, smaller than 5 millimeters.

According to another aspect, there is provided a system comprising a device described above, a trocar and an endoscope, the trocar being held by the holding portion along the longitudinal center axis and the endoscope being inserted into the trocar and held by a force exerted by the bearing surfaces.

One of the aspects of the disclosure is that a clamping mechanism consisting of two holding elements is attached to a substantially arbitrary trocar. The two holding elements are mounted so as to be movable relative to the coupling element and may be rotated about the pivot axis. For this purpose, the holding elements may have a cylindrical or partially cylindrical projection or recess. Each of the individual holding elements in turn has a finger-like extension, the arm element, which in turn engages the instrument, in particular the endoscope (if necessary with an intermediate piece or guide element).

When the holding elements are pressed together mechanically, the pressure generated is transmitted to the instrument via the arm element, so that the instrument remains fixed in its current position. For this purpose, at least one of the two holding elements is mounted so that it may move. The coupling element itself may be rotated about an axis perpendicular to the pivot axis of the two holding elements. This causes the holding elements and thus also the trocar and the instrument to perform a pivoting movement around the intersection of both axes. In some embodiments, this point of intersection lies in the center of the trocar.

In an exemplary embodiment, the reaction force of the pressure of the holding elements may be used to fix the coupling element with respect to a stationary base. The system may be used with different trocars (possibly with an elastic holding element, e.g. an adapter sleeve) and may be used for different instruments (possibly with a guide element or with intermediate rings for different diameters).

The arm elements for transmitting the pressing force to the instrument, in particular the endoscope, may, in some exemplary embodiments, be configured to be removable or be mounted on the base elements so that the arm elements may be folded outwards. In some exemplary embodiments, the arm elements are firmly connected to the base elements. In this case the basic elements may, in some exemplary embodiments, be mounted with the arm elements on an intermediate adapter on the instrument.

After the trocar is placed, the holding elements may be assembled around it. For this purpose, there may be elements which, once they have been assembled, make the holding elements into a self-contained unit. These elements may consist of e.g. grooves, thorns or spring like elements.

In the next step, the single or multi-part coupling element may be placed around the holding elements, folded or pushed on, depending on the desired embodiment. In a final step, an activator, which may be a pneumatic piston, a piezo actuator or an electric motor, for example, is then, in some exemplary embodiments, connected to the pushing element, and if necessary also to the coupling element.

One of the objectives is to enable the surgeon, by means of a suitable mechanical rotation and holding mechanism, to move an instrument, in particular an endoscope, inserted into a trocar in the axial direction by simply releasing this mechanism, and to enable rotation about a pivot point. After closing the mechanism, both the instrument and the trocar should be fixed in the set position. The entire holding system should fit smoothly into the familiar surgical procedure and be easy to assemble and disassemble. The mechanism may be fixed to a conventional holding arm, for example. Opening and closing of the mechanism may be possible, in some exemplary embodiments, with one hand and, in other exemplary embodiments, via a suitable remote control, which may be attached to the endoscope or instrument, for example.

It goes without saying that the features mentioned above and those to be explained below may be used not only in the combination indicated in each case, but also in other combinations or on their own, without leaving the spirit and the scope of the present disclosure.

Figure 2:
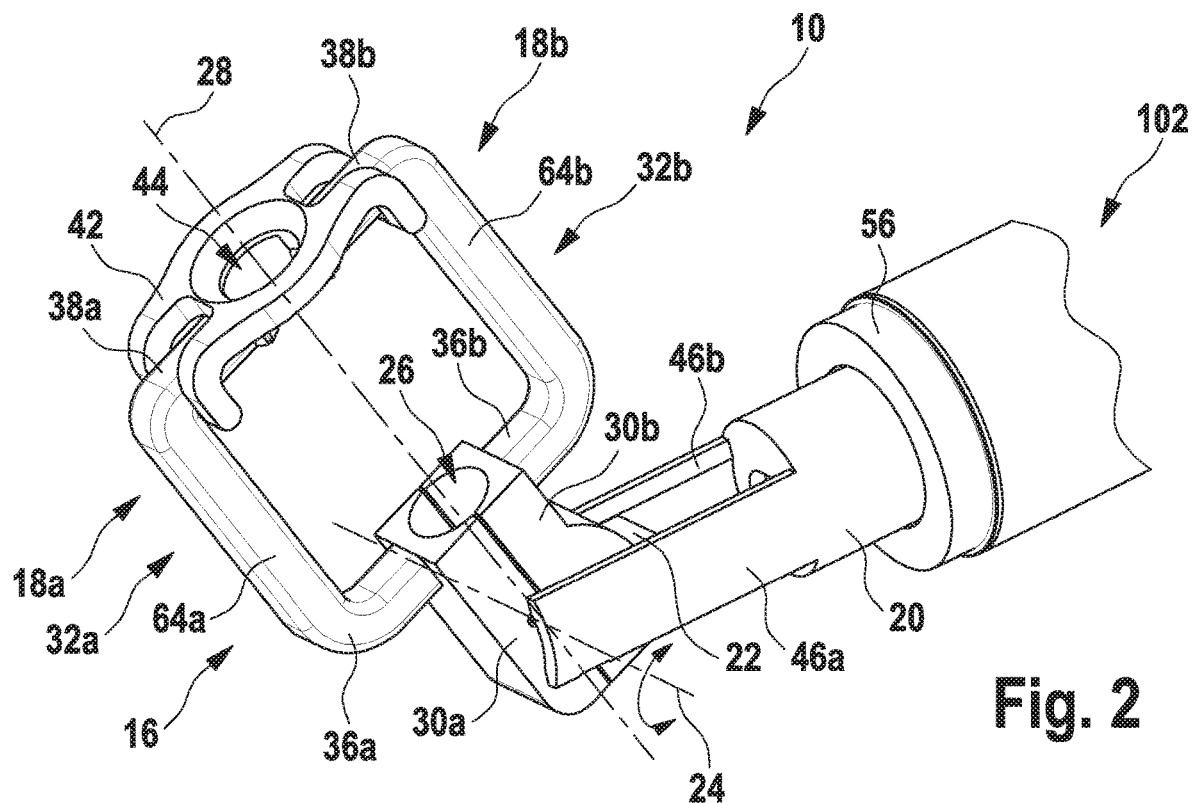
Figure 3:
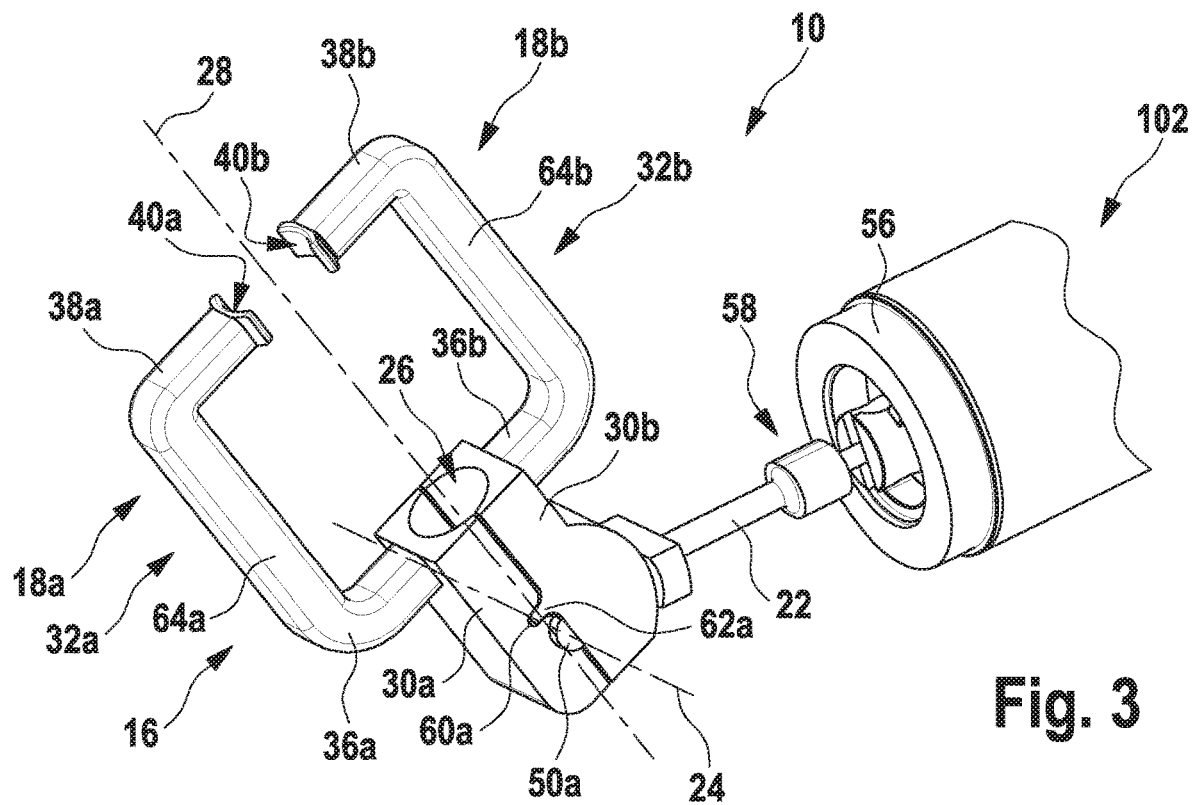
Figure 4:
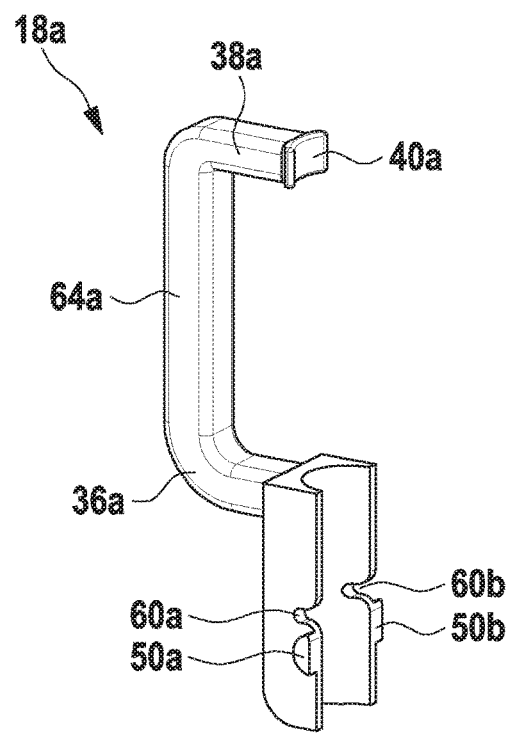
Figure 5:
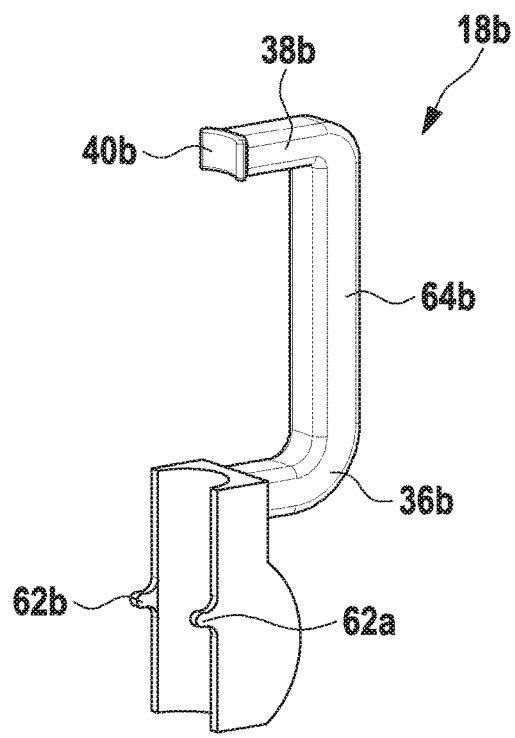
Figure 6:
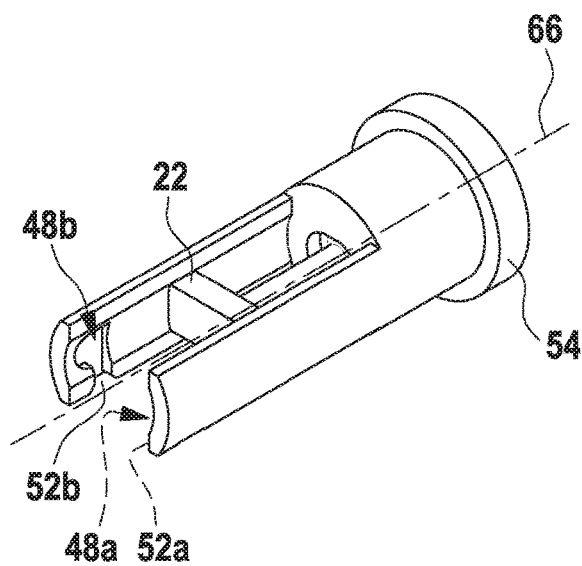

Exemplary embodiments of the disclosure are shown in more detail in the drawing and are explained in the following description. Shown it:

FIG. 1 a holding device with a system coupled to it;
FIG. 2 an exemplary embodiment of the device;
FIG. 3 the exemplary embodiment according to FIG. 2, whereby the guide element and the coupling element have been removed;
FIG. 4 a first holding element of the two holding elements from FIG. 2;
FIG. 5 a second holding element of the two holding elements from FIG. 2;
FIG. 6 the pushing element and the coupling element from FIG. 2 from a first perspective; and
FIG. 7 the pushing element, the coupling element and the union element from FIG. 2 from a second perspective.

FIG. 1 shows an apparatus 100, which has a holding arm 102 and a system 104. System 104 has an apparatus 10 which fixes a first medical instrument 12, here a trocar, and a second medical instrument 14, here an endoscope. The device 10 will now be explained in more detail below.

FIG. 2 shows the device 10 for simultaneous fixation of medical instruments 12, 14 from FIG. 1. The device 10 has a holding portion 16 which has two holding elements 18a, 18b, a coupling element 20, and a pushing element 22 (see also FIG. 3). The coupling element 20 is configured so that the holding portion 16 may be pivoted about a pivot axis 24 in a pivot plane, which is symbolically indicated by the double arrow. The pushing element 22 here has the shape of a pusher.

The pushing element 22 is configured to exert in a first position no force or a first force on the holding portion 16 so that the holding portion 16 may be pivoted, and in a second position a second force, which is greater than the first force, on the holding portion 16 so that the holding portion 16 is fixed with respect to a rotation about the pivot axis, i.e. in the pivot plane. The holding portion 16 has a continuous cavity 26 with a longitudinal center axis 28, which is configured to receive the first medical instrument 12 along the longitudinal center axis 28.

Each of the holding elements 18a, 18b has a corresponding base element 30a, 30b and an arm element 32a, 32b, each arm element 32a, 32b having a first arm section 36a, 36b starting from base element 30a, 30b and extending away from the longitudinal center axis 28, and a second arm section 38a, 38b approaching the longitudinal center axis 28 and ending with a bearing surface 40a, 40b, thus forming a free space between the arm elements 32a, 32b, which is configured to accommodate the second medical instrument 14 along the longitudinal center axis 28.

The pushing element 22 is configured to press a second holding element 18b of the holding elements 18a, 18b against a first holding element 18a of the holding elements 18a, 18b, whereby the bearing surface 40a of the first holding element 18a and the bearing surface 40b of the second holding element 18b also move towards each other.

The device 10 further comprises a guide element 42 which has an opening 44 arranged perpendicular to the longitudinal center axis 28, the guide element 42 resting against the bearing surfaces 40a, 40b at least when the second force acts on the holding portion 16.

Coupling element 20 has two projections 46a, 46b, which are parallel to each other and between which pushing element 22 is guided, here guided in a recess in each case. The coupling element 20 also has two recesses 48a, 48b (see FIG. 6) which face each other, the holding portion 16 having on each of two opposite sides a projection 50a, 50b (see FIG. 4) which engages in one of the recesses 48a, 48b.

The recesses 48a, 48b each have a slot 52a, 52b, which is configured in such a way that the holding portion 16 may be pushed out of the recesses 48a, 48b perpendicular to the pivot axis 24. In some exemplary embodiments, the projections 50a, 50b then have a semi-cylindrical shape. Furthermore, it can be seen that the longitudinal center axis 28 intersects the pivot axis 24.

The holding arm 102 holds or supports the pushing element 22 when the second force is applied. The coupling element 20 has a flange 54 (see FIG. 6), which is attached to the holding arm 102 with a union element 56 (see FIG. 7).

FIG. 3 shows again the embodiment as shown in FIG. 2, but the guide-element 42 and the coupling element 20 are not shown. It can be seen that the pushing element 22 is coupled to the holding arm 102 via a ball joint 58. An actuator (not shown) is located in the holding arm 102, in particular an electric motor, with which the pushing element 22 may be moved back and forth between at least the first position and the second position.

The first holding element 18a of the holding elements 18a, 18b has two recesses 60a, 60b and the second holding element 18b of the holding elements 18a, 18b has two projections 62a, 62b, the respective projection 62a, 62b engaging in the respective recess 60a, 60b at least when the second force acts on the holding portion 16.

Each arm element 32a, 32b has a third arm section 64a, 64b which is arranged between the respective first arm section 36a, 36b and the respective second arm section 38a, 38b and in particular extends at least substantially parallel to the longitudinal center axis 28. In particular, the respective first arm section 36a, 36b and the respective second arm section 38a, 38b are each at least substantially perpendicular to the third arm section 64a, 64b.

The holding portion 16 is configured to guide a trocar and the support surfaces 40a, 40b are configured to hold an endoscope inserted into the trocar.

FIG. 4 shows the first holding element 18a of the two holding elements 18a, 18b of FIG. 2. The projections 50a, 50b and the recesses 60a, 60b are clearly visible here.

FIG. 5 shows the second holding element 18b of the two holding elements 18a, 18b from FIG. 2 The projections 62a, 62b are clearly visible here. The second holding element 18b has a rounding in its section which interacts with the pushing element 22 so that the holding portion 16 may slide along the pushing element 22 when it is displaced.

FIG. 6 shows the pushing element 22 and the coupling element 20 from FIG. 2 from a first perspective. The recess 48b with the slot 52b is clearly visible. The recess 48a with the slot 52a is covered in this perspective.

Figure 7:
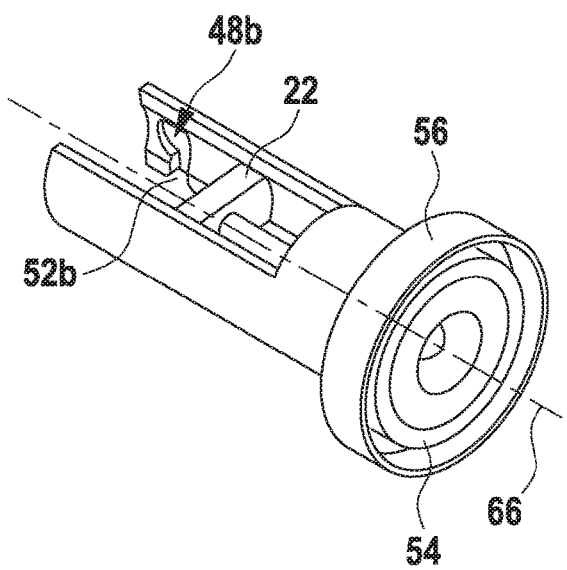

FIG. 7 shows the pushing element 22, the coupling element 20 and the union element 56 from FIG. 2 from a second perspective.

The invention claimed is:

1. A device configured for simultaneous fixation of medical instruments, the device comprising:
 a holding portion having two holding elements,
 a coupling element, and
 a pushing element, wherein the coupling element is configured so that the holding portion is pivotable about a pivot axis, and the pushing element is configured, in a first position, so that the holding portion can be pivoted, and, in a second position, to exert a force on the holding portion so that the holding portion is rotationally fixed around the pivot axis, the holding portion comprising a continuous cavity having a longitudinal center axis and configured to receive a first medical instrument along the longitudinal center axis, each of the holding elements comprising a base member and an arm member, each arm member having a first arm section starting from the base member extending away from the longitudinal center axis, and a second arm section approaching the longitudinal center axis and ending with a support surface, wherein a free space is located between the arm members, the free space configured for receiving a second medical instrument along the longitudinal center axis.

2. The device of claim 1, wherein the pushing element is configured to push a first holding element of the holding elements against a second holding element of the holding elements, wherein a bearing surface of the first holding element and a bearing surface of the second holding element are configured to move towards each other.

3. The device of claim 1, wherein the device further comprises a guide element having an opening arranged perpendicular to the longitudinal center axis, and the guide element abuts against bearing surfaces when the force acts on the holding portion.

4. The device of claim 1, wherein the coupling element includes two projections which are parallel to each other and between which the pushing element is guided.

5. The device of claim 1, wherein the coupling element includes two recesses facing each other, and wherein the holding portion includes, on two opposite sides, a respective projection which engages in one of the recesses.

6. The device of claim 5, wherein the recesses have a slot wherein the holding portion can be pushed out of the recesses perpendicularly to the pivot axis.

7. The device of claim 1, where the longitudinal center axis intersects the pivot axis.

8. The device of claim 1, further comprising a holding arm by which the pushing element is held when the force is exerted, wherein the coupling element includes a flange which is attached to the holding arm by a union element.

9. The device of claim 1, wherein the pushing element is coupled to the holding arm via a ball joint.

10. The device of claim 1, wherein a first holding element of the holding elements includes a recess and a second holding element of the holding elements includes a projection, the projection engaging the recess when the force acts on the holding portion.

11. The device of claim 1, each arm element having a third arm section which is arranged between the first arm section and the second arm section and in particular extends at least substantially parallel to the longitudinal center axis.

12. The device of claim 11, wherein the first arm section and the second arm section are each at least substantially perpendicular to the third arm section.

13. The device of claim 1, wherein an elastic holding element is inserted into the holding portion which is configured to receive a first instrument of the medical instruments along the longitudinal center axis.

14. The device of claim 1, wherein the holding portion is configured to guide a trocar and bearing surfaces are configured to hold an endoscope inserted into the trocar.

15. The device of claim 1, wherein the coupling element includes two projections facing each other, and wherein the holding portion includes on two opposite sides a respective recess in which one of the projections engages.

16. A system comprising the device of claim 1, a trocar and an endoscope, wherein the trocar is held by the holding portion along the longitudinal center axis and the endoscope is inserted into the trocar and held by a force exerted by bearing surfaces.

17. A device configured for simultaneous fixation of medical instruments, the device comprising:

a holding portion having two holding arms, the holding portion comprising a cavity having a longitudinal center axis and configured to receive a first medical instrument along the longitudinal center axis, each of the holding arms comprising a base member and an arm member, each arm member having a first arm section starting from the base member extending away from the longitudinal center axis, and a second arm section approaching the longitudinal center axis and ending with a support surface, wherein a free space is located between the arm members, the free space configured to receive a second medical instrument along the longitudinal center axis;

a coupling element; and a pushing element, wherein the coupling element is configured to rotationally hold the holding portion pivotable about a pivot axis, and the pushing element is configured, in a first position, so that the holding portion is pivotable, and, in a second position, to exert a fixing force on the holding portion so that the holding portion is rotationally fixed about the pivot axis.

* * * * *